United States Patent
Grove et al.

(10) Patent No.: US 8,755,420 B2
(45) Date of Patent: Jun. 17, 2014

(54) FAILURE PROTECTION APPARATUS AND SYSTEM

(75) Inventors: Robert E. Grove, Pleasanton, CA (US); Mark V. Weckwerth, Pleasanton, CA (US); Tobin C. Island, Oakland, CA (US); Harvey I. Liu, Fremont, CA (US)

(73) Assignee: Tria Beauty, Inc., Pleasanton, CA (US)

( * ) Notice: Subject to any disclaimer, the term of this patent is extended or adjusted under 35 U.S.C. 154(b) by 911 days.

(21) Appl. No.: 12/137,452

(22) Filed: Jun. 11, 2008

(65) Prior Publication Data

US 2009/0097513 A1 Apr. 16, 2009

Related U.S. Application Data

(60) Provisional application No. 60/944,086, filed on Jun. 14, 2007.

(51) Int. Cl.
*H01S 3/00* (2006.01)

(52) U.S. Cl.
USPC .................. 372/38.09; 372/38.01; 372/38.02; 372/38.07

(58) Field of Classification Search
CPC . H01S 5/0427; H01S 5/0428; H01S 5/06223; H01S 5/06808; H01S 5/06812
USPC ...................... 372/38.09, 38.01, 38.02, 38.07
See application file for complete search history.

(56) References Cited

U.S. PATENT DOCUMENTS

| | | | |
|---|---|---|---|
| 4,240,738 A | 12/1980 | Praamsma | |
| 4,684,883 A * | 8/1987 | Ackerman et al. | 324/71.5 |
| 5,295,052 A | 3/1994 | Chin et al. | |
| 5,756,981 A * | 5/1998 | Roustaei et al. | 235/462.42 |
| 6,536,914 B2 | 3/2003 | Hoelen et al. | |
| 7,068,910 B2 | 6/2006 | Duine et al. | |
| 2001/0046131 A1 | 11/2001 | Hoelen et al. | |
| 2003/0080755 A1 | 5/2003 | Kobayashi | |
| 2004/0120151 A1 | 6/2004 | Ostler et al. | |
| 2004/0167501 A1* | 8/2004 | Island et al. | 606/9 |
| 2005/0276072 A1 | 12/2005 | Hayashi et al. | |
| 2006/0206103 A1 | 9/2006 | Altshuler et al. | |
| 2006/0291510 A1* | 12/2006 | Juluri | 372/29.021 |
| 2007/0129711 A1 | 6/2007 | Altshuler et al. | |

* cited by examiner

*Primary Examiner* — Tod T Van Roy
(74) *Attorney, Agent, or Firm* — King & Spalding L.L.P.

(57) ABSTRACT

A safety and interlock circuit for use with devices which could cause injury if an error condition causes improper operation. A control program executing on a processor monitors a variety of device conditions, including pulse overduration threshold, diode over-current threshold, pulse lockout duration, temperature threshold, and pulse repetition frequency limit, and prevents the laser from firing if an error condition is detected. In addition, the error conditions are logged in a persistent memory to facilitate subsequent diagnosis and correction.

17 Claims, 1 Drawing Sheet

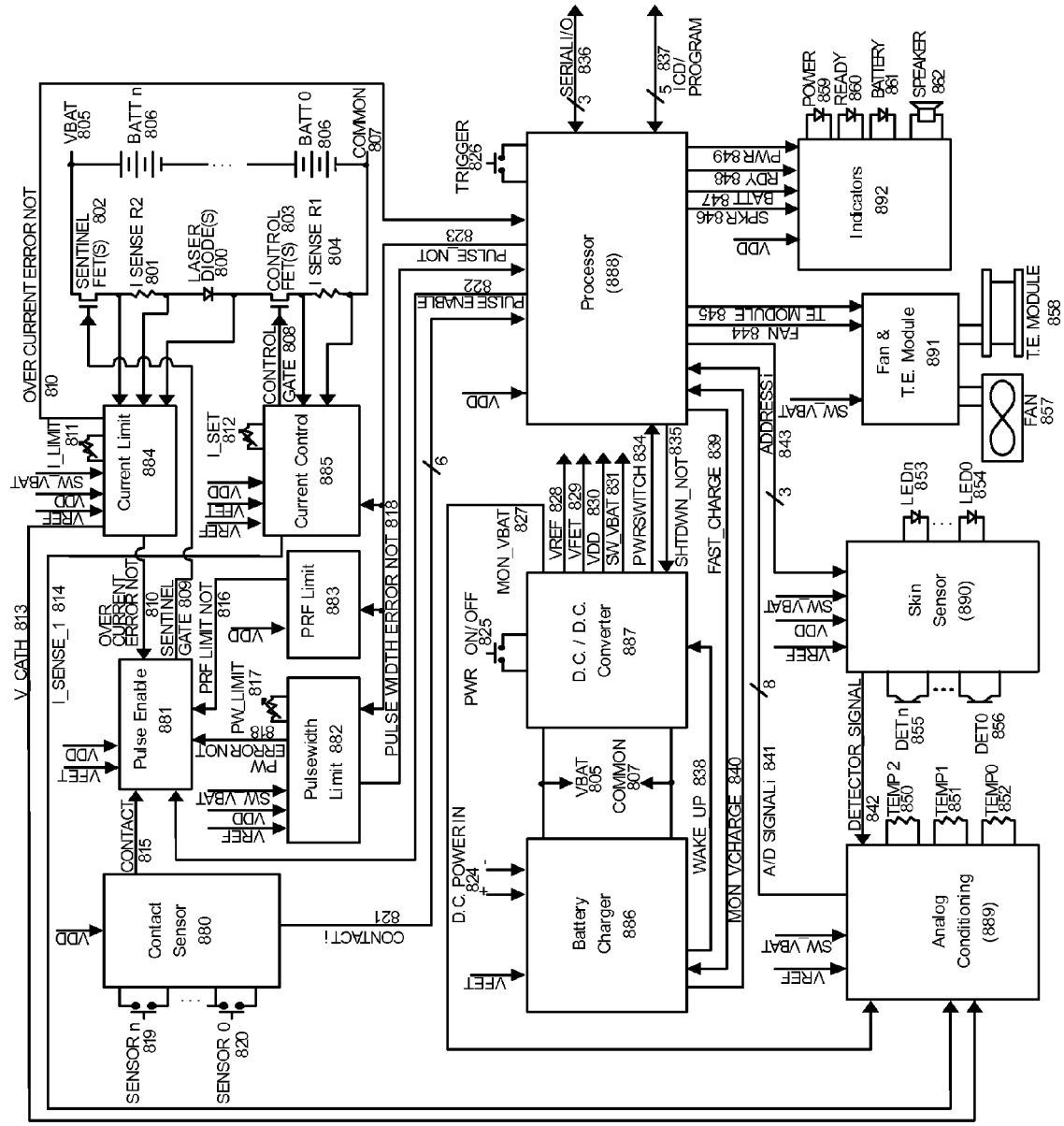

FAILURE PROTECTION APPARATUS AND SYSTEM

RELATED APPLICATION

This application claims the benefit of provisional U.S. Patent Application Ser. No. 60/944,086, filed Jun. 14, 2007, and incorporated herein by reference.

FIELD OF THE INVENTION

The present invention relates generally to interlock and related safety circuits, and more particularly relates to interlock and related safety circuits suited for use with laser-based medical devices.

BACKGROUND OF THE INVENTION

Medical devices, and any other device which could injure persons or property, require careful constraints to prevent such injury. This is particularly true for devices which will be used at home without supervision by a trained professional. While numerous approaches are known in the art, most involve complicated and expensive mechanical and electro-mechanical interlocks, which are either unworkable or unduly costly for devices intended for consumer use in the home.

In the case of laser-power medical devices, it is desirable to insure that the laser cannot fire except in an acceptable manner, and at an acceptable time, even if other safety measures also exist.

Thus, there has been a need for a design of interlock and safety circuits which prevent improper operation of laser-based devices

SUMMARY OF THE INVENTION

The present invention comprises a plurality of safety features embodied in hardware and/or software and particularly suited to use with a laser-power medical device, such as, for example, a laser-based device for performing cosmetic and dermatological procedures. Such safety features are particularly desirable when the laser-based device is intended for home use by consumers, where no expert, such as a physician, is overseeing the use of the device. In the case of a laser-based device, one technique for preventing injury is to prevent the firing of the lasers.

It is also desirable that the safety features operate independently, such that each safety feature can detect a malfunction elsewhere in the device that might result in injury to a patient, and, upon such detection, prevent the use of the device. Therefore, it will be appreciated by those skilled in the art the that, while all of the features described herein could be used in a single system, those features could also be used separately or in combinations comprising less than all of the features disclosed hereafter.

The foregoing advantages, as well as numerous others, can be appreciated from the following detailed description of the invention taken together with the appended FIGURE.

THE FIGURE

FIG. 1 illustrates in schematic block diagram form a control circuit for a laser-based medical device having the hardware interlocks which comprise an aspect of the present invention.

DETAILED DESCRIPTION OF THE INVENTION

Referring first to FIG. 1, several safety features comprising different aspects of the present invention can be appreciated. It will, in particular, be appreciated that these features operate substantially independently of the remainder of the circuitry, and also substantially independently of the software features described hereinafter or even corrupted software that would ordinarily control the laser emissions. These safety features can, if any of them detects a fault, "override" other control signals and prevent the lasers from being fired. Each of the following three circuits can be considered as limiting the laser emission, and are in addition to the circuits that control the laser emission. At the same time, the software features discussed hereinafter have, as one of their purposes, the monitoring of these hardware circuits for the purpose of determining that they are functioning properly. Thus, it will be appreciated that any defect discovered by either the hardware features discussed below or the software features discussed hereinafter can prevent laser emission, such that the lasers are permitted to emit only when all circuits are determined to be operating properly.

There exists an electronic circuit to monitor and limit the current flowing through the laser diodes. In particular, and again referring to FIG. 1, an over-current, or current limit circuit 884 continuously monitors the current flowing through the laser diodes, and has current sense resistor 801 which is independent of the current sense resistor associated with the current control circuit 885 and its associated sense resistor 804.

The control circuit 885 drives a field effect transistor (FET) referred to as the control FET that controls the amount of current flowing through the laser diodes 800, which in some implementations will comprise a plurality of laser diode bars, or may comprise one or more discrete laser diodes. If the over-current circuit 884 detects current flowing through the laser diodes greater than that permitted by a limit resistor 811, the over-current circuit sends a signal to a pulse enable circuit 881 that turns off a second FET referred to as the sentinel FET 802. The sentinel FET 802 is in series with the laser diodes and control FET. The limit resistor can be, depending upon the embodiment, a variable resistor, a fixed resistor. Alternatively, an A/D converter controlled by an additional microprocessor can be used to set the limit. In the event an over-current condition is detected, the over-current circuit 884 also sends a signal to the processor so that the processor can terminate the pulse and so the software can know that an error condition exists. The software will enter a fault mode. The operation of the device once the software enters a fault mode depends upon the particular implementation, and can range from retrying the control signals, to entering a recovery mode, to permitting only diagnostics, to completely ceasing to function until returned to for repair.

A second safety circuit, Pulsewidth Limit 882, monitors and limits the pulse duration of the laser emission. Just as the current limit circuit 884 operates independently from its associated current control circuit 885, so the Pulsewidth Limit 882 operates independently from the processor signals that normally control pulsewidth. The Pulsewidth limit, or pulse over-duration, circuit 882 monitors the duration of the signal 822 from processor 888 requesting a pulse. If the request has been on longer than a preset limit, set for example by pulsewidth limit resistor 817, the Pulsewidth Limit circuit sends a signal to the Pulsewidth Enable circuit 881 that turns off the sentinel FET 802, as before. In addition, if a pulsewidth error is detected, the over-duration circuit also sends a signal to the processor so that the processor can attempt to terminate the pulse control and so the software can know that an error condition exists. Again, the software will enter a fault mode.

In addition, a further safety circuit, the PRF Limit circuit 883, limits the pulse repetition frequency (PRF) of the device, or, how frequently a laser emission can occur. The PRF of the device is normally controlled by the pulse control program operating in the processor 888, which provides a pulse enable signal 822 to the pulse enable circuit 881 and drives the pulse not signal 823 low to request that a pulse be delivered. For example, the PRF Limit circuit 883 can be set to limit the PRF of the device so that no laser emission is possible for a period ranging from a few hundred milliseconds to several seconds after termination of a pulse. In an embodiment, the lockout period can be on the order of 900 ms after the termination of a pulse. Typically, a nominal pulse repetition frequency will be programmed into the control program operating in the processor 888, and the PRF Limit circuit will impose a somewhat faster maximum repetition rate. Thus, in an embodiment, the nominal PRF may be on the order of one pulse every two seconds, whereas the PRF Limit circuit 883 may enforce a limit of no more than one pulse approximately every second. Those skilled in the art will recognize that the exact limit for both the PRF and the PRF Limit can vary within a substantial range depending upon the implementation, and can be between a few milliseconds and a few seconds.

Each circuit, control and PRF, typically has an independent time base. The control circuit drives the control FET 803. The PRF circuit prevents the sentinel FET 802 from turning on by providing an enable signal 818 to the Pulse Enable circuit 881 only after the lockout period has ended. The PLO circuit also signals the processor so that the software can know when the pulse has been "locked-out". In the event the control program attempted to initiate a pulse during the lockout period, the software can be caused to enter a fault mode, depending upon the particular embodiment. In an embodiment found to be suitable for certain laser devices for dermatological treatments, the PLO circuit and enable circuit, together, can limit the PRF to 1.11 Hz for infinitely short pulses and can limit the PRF to 0.645 Hz for long pulses, independently of the control program.

In an alternative arrangement, a second processor can be implemented for monitoring pulse duration, diode current, and PRF. As a further alternative, the over-duration threshold, over-current threshold, and pulse lock-out duration can be programmable so that each device is permitted to emit only a specific amount of energy above the nominal amount for that specific device. This permits adjustment of the thresholds to take into account the variation of light output that occurs in different laser diodes and laser diode bars. For example, a particular device can be programmed to output a specified amount of light during the calibration process done during manufacturing. This can be achieved, in at least some embodiments, by adjustment of the pulsewidth to be either slightly shorter or slightly longer than the nominal pulsewidth. That data is then used to establish a programmable threshold, so that the light output does not exceed, for example, 110% of the nominal output. Those skilled in the art will appreciate that the exact thresholds set by the above-described limiting circuits can vary over a significant range, depending upon the implementation.

In addition to the foregoing safety features that limit the laser emissions, temperature monitoring can also be provided to ensure that the device operates within acceptable limits. Thus, in an embodiment, one or more temperature sensors can be provided, to monitor the temperature of (1) the mixer/barrel/tip assembly, (2) the laser diodes and the heatsink upon which they are typically mounted, and (3) the battery/main circuit board. Resettable thermal fuses and a thermal cut-off (TCO) can also be provided which are activated in the event of over-temperature conditions.

Under normal use of the device, the mixer/barrel/tip assembly will heat. This heating can occur due to normal light scattering in the device, and can also occur because the tip assembly essentially attempts to serve as a heatsink for the skin contacted by the tip. The mixer/barrel/tip assembly temperature is monitored with a thermistor. The signal generated by the thermistor is monitored in the processor 888, and the control program within the processor turns on heat-reducing devices such as TE modules 891 in the event that the temperature of the mixer/barrel/tip assembly exceeds a threshold, for example 33° C. The exact threshold temperature can be adjusted over a wide range above and below ambient.

The diode/heatsink temperature is also monitored with a thermistor that provides a signal to the processor 888. The control program, or software, operating in processor turns on a fan or other heat ejection devices in the event that the temperature of the diode/finned heatsink assembly reaches a threshold. Similarly, the temperature of the battery/main circuit board is monitored by the use of a thermistor, which provides a signal to the processor 888 that is monitored by the control program. In an embodiment, a temperature threshold applicable during laser emissions can be set separately from the threshold applicable during charging of the batteries, although the separate thresholds are not required for all embodiments. For example, the circuit board threshold can be nominally 60° C. during laser emission, achievable by limiting the PRF appropriately including prohibiting the emission of any pulses. The software can likewise limit the temperature of the battery/main circuit board during charging to a present threshold temperature by limiting the charging current to a value less than the maximum 2 A or if necessary, by turning off the charging.

In an embodiment, one or more resettable thermal fuses are used to limit the charge current drawn by the device in the event of a failure and to limit the current drawn by the electrical circuits from the battery in the event of a failure. These fuses are also sensitive to excess heat. If the electronics in the vicinity of the charging circuit and in the vicinity of the FET's and in the vicinity of the laser diodes gets too hot the resettable thermal fuses may activate and limit the current.

A thermal cut-off device is placed in the vicinity of the battery. In the event that the battery is overcharged or for some other reason gets too hot, the TCO will activate to open the circuit used to charge the battery.

To ensure good thermal coupling between the thermistor and the object whose temperature is being measured, such as the diodes and heatsink, an aluminum screw and copper pours on the circuit board are used in at least some embodiments. In an embodiment, surface mount thermistors are mounted on the associated circuit board. The portion of the circuit board where the thermistors are mounted is thermally coupled to the assembly whose temperature is to be monitored. One implementation is to mount the thermistor on a portion of the board very near to a screw hole used to attach the board to the assembly. The layers of the circuit board underneath the location of the thermistor have a copper pour (a sheet of copper) that encircles the screw hole. An aluminum screw is placed through the hole and turned into the assembly whose temperature is to be measured. Heat flows through the screw (or directly into the bottom surface of the board), flows laterally through the copper pours, to within a few thousandths of an inch of the thermistor. The heat flows the final few thousandths of an inch through the FR4 material of the circuit board into the thermistor.

This enables the thermistor to be assembled onto the board with conventional board assembly machines at the same time as all of the other electronic components. The thermistor can be tested in the circuit prior to the board being assembled into the device. The same hole and screw that is used to mount the board to the device is also the screw and hole that thermally shorts the thermistor to the device. No wires are needed to connect the thermistor, resulting in an inexpensive and highly reliable implementation.

Two inexpensive, reliable, easy to manufacture 40 A electrical connections must be made to the laser diode package (one to the anode and one to the cathode). In an embodiment, the anode and the cathode are connected in two different ways.

The connection to the anode was made by providing a top surface on the laser diode package that is large, flat, electrically conductive, and electrically shorted to the laser diode anode. The FET circuit board (the board that controls the diode current) was designed to have a large, flat, electrically conductive region that can be held in contact with the previously mentioned region on the diode package. A screw and a belville washer are used to compress the circuit board against the diode package. The connection to the cathode of the laser diode package was made by shorting the cathode of the laser diode package to the heatsink. Current passing through the laser diode package can then pass into the heatsink. In an embodiment, one of the FET packages used to control the laser diode current is thermally shorted to the heatsink to prevent the FET from overheating. The flange of the FET package that is screwed to the heatsink is purposely not electrically insulated from the heatsink. The flange of this FET package serves as one of the three electrical terminals of the transistor within the package. Therefore, by shorting the cathode to the heatsink, and by shorting the flange of the FET package to the heatsink, the heatsink can be a part of the electrical circuit passing the 40 A. Current can pass from the cathode of the laser diode into the heatsink and into the flange of the FET package.

In addition to the hardware safety features described above, software-based safety features can also be implemented in various embodiments of the invention. As previously noted, although these features operate independently and can be separately implemented, some embodiments can include all or nearly all of the features described herein.

In some embodiments, an activation process is required to unlock the device prior to use. In an embodiment, the unlock process requires that the power button be pressed and held for an extended period, on the order of a several seconds, until a series of beeps are emitted from the device, at which point the device is unlocked. In some embodiments, an additional step is implemented wherein the power button must be released after the correct number of beeps. In an alternative embodiment, particularly suited to laser hair removal devices, pressing and holding the power button activates a skin sensor, and the device is unlocked by placing the device against the skin so that the skin sensor can determine skin color. If the skin color is too dark, such that a risk of injury might exist if the device were used, the device will not unlock. However, for skin color that is not likely to be injured, the device will unlock. As a further alternative, hair color may be detected in combination with skin color, and the device will only unlock if a suitable contrast exists between the color of the hair and the color of the skin, since laser hair removal devices may not be effective on persons with very light hair. As a still further alternative, the skin color sensor can adjust the output fluence of the device in accordance with skin color, for example by limiting the pulsewidth for the subsequent shot. In such an arrangement, where the skin color sensor is integrated into the device, skin color can be detected, and output fluence adjusted, with every shot. This permits the device to automatically accommodate variations in skin color across the body, such as caused by tan lines, while still allowing a safe but effective treatment at each site. In a still further alternative embodiment, an external skin color sensor can be implemented, which is similar to the integrated skin sensor described above except that the external skin sensor transmits to the device a signal representative of the skin color, in response to which the device either unlocks or sets output fluence, depending upon the embodiment. Where an external device is used, a plurality of LED's of different wavelengths are used to illuminate the target area, to minimize the possibility that objects other than the patient's skin are being illuminated in an attempt to trick the device.

During device startup, the control program operating in the processor tests the function of the PRF Limit circuit 883 (FIG. 1). An aspect of this test is that the function of the PRF Limit circuit is tested without pulsing the lasers. In operation, the software signals the Pulse Enable circuit 881 to enable a laser pulse, while at the same time signaling the current control circuit 885 to send zero current through the laser diodes. The triggering of the laser pulse activates the PRF circuit, and the software can then measure and confirm the proper duration of the lock-out, indicating that the PRF Limit circuit is operating properly.

An additional software-based safety features monitors the diode current during operation. The current control circuit 885 senses, amplifies, and scales the diode current and provides a proportional signal to the processor through conditioning circuit 889. The control program in the processor can then know the amount of current flowing through the device in real-time. Because of non-idealities in electrical components the signal to the processor will not be exactly zero even when no current is flowing through the diodes. During start-up when no current is flowing through the diodes, the software control program ensures that this zero "offset" is below a predetermined threshold, to ensure that the laser emissions are safe but effective. If the offset is excessive, then something is likely wrong with the device and the software enters a "fault mode".

A further software-based safety feature confirms that the Pulsewidth Limit circuit 882 is operating properly. During start-up, the software can request a "phantom" laser pulse during which no current is provided to the laser diodes so there is no laser emission, as described above. The software purposefully requests a pulse of duration long enough to exceed the predetermined threshold at which the Pulsewidth Limit circuit 882 should activate. By monitoring if and when the processor is notified the software can determine if the over-pulse duration circuitry is working and confirm the time of the predetermined threshold. If the processor is not notified, or if it is notified but the duration is too short or too long, then the software enters a "fault mode". The time base for the over-pulse duration circuitry is independent of the time base for the control of the pulse duration. This means that both of the "clocks" must be working correctly for the device to function.

A still further software safety feature confirms the functioning of the Current Limit circuitry 884. During start-up, the software can request a laser pulse with a current low enough to be below the threshold for lasing. So, despite the fact that current is flowing through the laser diodes there is no laser emission. The software can also request that the threshold maximum current be lowered below this lower laser diode current. In this case, the threshold for maximum current should be exceeded even though the amount of current flowing through the laser diodes is below the threshold current for lasing. By monitoring whether or not the processor is notified, the software determines whether the Current Limit circuitry is working without the need to emit any laser emission. If the processor is not notified of an over-current condition then the software enters a "fault mode".

In a still further software-based safety feature, the control program operating in the processor 888 confirms the functioning of the Sentinel FET 802. As noted above, the sentinel FET 802 is in series with the control FET 803 and functions to turn off current flow to the laser diodes during fault conditions. If the control FET fails such that it cannot control the current then the sentinel FET can turn off the current. If the sentinel FET fails, then the control FET can turn off the current.

The current limit circuit 884 provides to the processor a signal 813 (FIG. 1) that allows the software to monitor the voltage of the laser diode cathode terminal. By monitoring the cathode voltage the software can determine if the sentinel FET has failed such that it cannot turn off the current. The cathode voltage will indicate a failed sentinel FET even if the control FET is off. In this way, the sentinel FET can be confirmed to be capable of opening the diode current loop even without turning on the control FET and causing laser emission. If the software determines that the sentinel FET is not functioning, then the device enters a "fault mode".

An additional software-based test confirms that the diode forward voltage is correct. When the sentinel FET is turned on, the battery voltage is very nearly the same as the laser diode anode voltage. The difference between the laser diode anode voltage and the laser diode cathode voltage is the laser diode forward voltage. These voltages are supplied to the processor, such that the software can calculate the approximate laser diode forward voltage from the battery voltage and the cathode voltage. The laser diode forward voltage will increase with increasing laser diode current. When the sentinel FET is on and the control FET is off, the electronic circuitry provides for a small laser diode current to flow (well below the lasing threshold of the laser diodes). Even though there is no laser emission the laser diode forward voltage (at low current) may be measured by turning on the sentinel FET and turning off the control FET. The magnitude of the forward voltage can be used to determine if the electronic circuitry is working properly. If the laser diode voltage is too low, it may indicate that one of the laser diode bars is not working which may result in low optical power output and ineffective treatment.

As noted above, the control program monitors the laser diode current, so that the software knows the amount of current flowing through the device in real time. Between pulses, the control program continuously monitors the laser diode current. If current above some threshold is detected then the software will enter a "fault mode", since unintended laser diode current could indicate unintended laser emission.

A further software-based safety feature involves reducing the hardware current setpoint to a low current after each pulse, where that interim setpoint is below the laser emission threshold. In the case that the sentinel FET and control FET are inadvertently enabled, the laser will not emit any radiation.

In addition, the software control program stores in the device data gathered from the most recent laser emission, as well as information gathered during the sum of all pulses. In the event of a device failure, this information provides a history of the device which can prove extremely helpful during diagnostics, including permitting the manufacturer of the device to more quickly repair the device, and also to recognize issues that may arise in other devices.

In the event that either a software failure or a hardware failure causes the device to enter a fault condition, at least some embodiments of the invention cause one or more of the following to occur: (1) the TE module is turned off, (2) the laser diode current is interrupted, indicators are activated to indicate to the user that the device has entered a fault state, and context sensitive parameters are stored in persistent data. In addition, the device must, in at least some embodiments, be power recycled to be reset. Should the device enter the fault mode again, the number of times a failure occurs is also entered into persistent data to assist in diagnostics.

In an additional feature, the present invention includes, in some embodiments, storing within the device a log of some or all of the safety testing performed in the factory. This reduces the chance for human error in filling out paper travelers that would otherwise keep track of testing/calibration performed on the device.

Having fully described a preferred embodiment of the invention and various alternatives, those skilled in the art will recognize, given the teachings herein, that numerous alternatives and equivalents exist which do not depart from the invention. It is therefore intended that the invention not be limited by the foregoing description, but only by the appended claims.

We claim:

1. A circuit for limiting the operation of a laser-based device comprising:
   at least one laser diode,
   one or more safety circuits that detect fault conditions associated with laser pulses emitted by the at least one laser diode according to one or more pulse emission parameters, including at least one of: (a) a current limit circuit configured to detect an over-current fault condition associated with one or more emitted laser pulses, (b) a pulsewidth, limit circuit configured to detect a pulse duration fault condition associated with one or more emitted laser pulses, and (c) a pulse repetition frequency limit circuit configured to detect a pulse frequency fault condition associated with one or more emitted laser pulses,
   an interlock circuit responsive to any of the fault conditions associated with one or more emitted laser pulses for preventing the at least one laser diode from emitting a subsequent laser pulse or for terminating an ongoing laser pulse, and
   a safety circuit testing system that alters at least one of the pulse emission parameters in order to test whether at least one of the safety circuits that detects fault conditions associated with laser pulses emitted by the at least one laser diode is operating properly, wherein the testing performed by the safety circuit testing system is performed without emitting a laser pulse and independent of any emission by the at least one laser diode.

2. The circuit of claim 1 further comprising control logic to cause the device to enter a fault mode further comprising a log for recording errors.

3. The circuit of claim 1, wherein:
   the current limit circuit detects an over-current fault condition, and
   the safety circuit testing system tests whether the current limit circuit is operating properly, by:
      lowering a current limit threshold below a current level required for generating a laser pulse, requesting a laser pulse with a current above the lowered current limit threshold but below the current level required for generating a laser pulse, and determining whether a notification signal is generated in response to the requested laser pulse current exceeding the lowered current limit threshold, wherein the notification signal is generated if the current limit circuit is working properly and not generated if the current limit circuit is not working properly.

4. The circuit of claim 1, wherein:

the pulse width limit circuit detects a pulse duration fault condition, and the safety circuit testing system tests whether the pulsewidth limit circuit is operating properly, by:

requesting a phantom laser pulse that does not trigger an actual laser pulse, the requesting a phantom laser pulse having a duration exceeding a preset pulsewidth threshold, determining whether a notification signal is generated in response to the requested phantom laser pulse having a duration exceeding the preset pulsewidth threshold, wherein the notification signal is generated if the pulsewidth limit circuit is working properly and not generated if the pulsewidth limit circuit is not working properly.

5. The circuit of claim 1, wherein:

the pulse repetition frequency limit circuit detects a pulse frequency fault condition, and the safety circuit testing system tests whether the pulse repetition frequency limit circuit is operating properly, by:

generating a first signal to trigger a laser pulse, and a second signal to send zero current through the at least one laser diode, such that no laser pulse is actually emitted, determining the duration of a pulse lock period following the triggered laser pulse, determining whether the pulse repetition frequency limit circuit is operating properly based on the determined duration of the pulse lock period following the triggered laser pulse.

6. The circuit of claim 1 wherein the one or more pulse emission parameters include a signal for triggering a laser pulse and a current supplied to the at least one laser diode for generating a laser pulse.

7. A circuit for limiting the operation of a laser-based device comprising:

at least one laser diode, one or more safety circuits that detect fault conditions associated with laser pulses emitted by the at least one laser diode according to one or more pulse emission parameters, including at least one of: (a) a pulsewidth limit circuit configured to detect a pulse duration fault condition associated with one or more emitted laser pulses, and (b) a pulse repetition frequency limit circuit configured to detect a pulse frequency fault condition associated with one or more emitted laser pulses, an interlock circuit responsive to any of the fault conditions associated with one or more emitted laser pulses for preventing the at least one laser diode from emitting a subsequent laser pulse or for terminating an ongoing laser pulse, and a safety circuit testing system that alters at least one of the pulse emission parameters in order to test whether at least one of the safety circuits that detects fault conditions associated with laser pulses emitted by the at least one laser diode is operating properly without supplying any current to the at least one laser diode.

8. The circuit of claim 7, further comprising control logic to cause the device to enter a fault mode further comprising a log for recording errors.

9. The circuit of claim 7, wherein:

the pulse width limit circuit detects a pulse duration fault condition, and the safety circuit testing system tests whether the pulsewidth limit circuit is operating properly, by:

requesting a phantom laser pulse that does not trigger an actual laser pulse, the requesting a phantom laser pulse having a duration exceeding a preset pulsewidth threshold, determining whether a notification signal is generated in response to the requested phantom laser pulse having a duration exceeding the preset pulsewidth threshold, wherein the notification signal is generated if the pulsewidth limit circuit is working properly and not generated if the pulsewidth limit circuit is not working properly.

10. The circuit of claim 7, wherein;

the pulse repetition frequency limit circuit detects a pulse frequency fault condition, and the safety circuit testing system tests whether the pulse repetition frequency limit circuit is operating properly, by:

generating a first signal to trigger a laser pulse, and a second signal to send zero current through the at least one laser diode, such that no laser pulse is actually emitted, determining the duration of a pulse lock period following the triggered laser pulse, determining whether the pulse repetition frequency limit circuit is operating properly based on the determined duration of the pulse lock period following the triggered laser pulse.

11. The circuit of claim 7, wherein the one or more pulse emission parameters include a signal for triggering a laser pulse and a current supplied to the at least one laser diode for generating a laser pulse.

12. A battery-powered, laser-based treatment device, comprising:

at least one laser diode, at least one battery configured to provide current to the at least one laser diode, one or more safety circuits that detect fault conditions associated with laser pulses emitted by the at least one laser diode according to one or more pulse emission parameters, including at least one of: (a) a current limit circuit configured to detect an over-current fault condition associated with one or more emitted laser pulses, (b) a pulsewidth limit circuit configured to detect a pulse duration fault condition associated with one or more emitted laser pulses, and (c) a pulse repetition frequency limit circuit configured to detect a pulse frequency fault condition associated with one or more emitted laser pulses, an interlock circuit responsive to any of the fault conditions associated with one or more emitted laser pulses for preventing the at least one laser diode from emitting a subsequent laser pulse or for terminating an ongoing laser pulse, and a safety circuit testing system that alters at least one of the pulse emission parameters in order to test whether at least one of the safety circuits that detects fault conditions associated with laser pulses emitted by the at least one laser diode is operating properly, wherein the testing performed by the safety circuit testing system is performed without emitting a laser pulse and independent of any emission by the at least one laser diode.

13. The device of claim 12, further comprising control logic to cause the device to enter a fault mode further comprising a log for recording errors.

14. The device of claim 12, wherein:

the current limit circuit detects an over-current fault condition, and the safety circuit testing system tests whether the current limit circuit is operating properly, by:

lowering a current limit threshold below a current level required for generating a laser pulse, requesting a laser pulse with a current above the lowered current limit threshold but below the current level required for generating a laser pulse, and determining whether a notification signal is generated in response to the requested laser pulse current exceeding the lowered current limit threshold, wherein the notification signal is generated if the current limit circuit is working properly and not generated if the current limit circuit is not working properly.

15. The device of claim 12, wherein:

the pulse width limit circuit detects a pulse duration fault condition, and the safety circuit testing system tests whether the pulsewidth limit circuit is operating properly, by:

requesting a phantom laser pulse that does not trigger an actual laser pulse, the requesting a phantom laser pulse having a duration exceeding a preset pulsewidth threshold, determining whether a notification signal is generated in response to the requested phantom laser pulse having a duration exceeding the preset pulsewidth threshold, wherein the notification signal is generated if the pulsewidth limit circuit is working properly and not generated if the pulsewidth limit circuit is not working properly.

16. The device of claim 12, wherein:

the pulse repetition frequency limit circuit detects a pulse frequency fault condition, and the safety circuit testing system tests whether the pulse repetition frequency limit circuit is operating properly, by:

generating a first signal to trigger a laser pulse, and a second signal to send zero current through the at least one laser diode, such that no laser pulse is actually emitted, determining the duration of a pulse lock period following the triggered laser pulse, determining whether the pulse repetition frequency limit circuit is operating properly based on the determined duration of the pulse lock period following the triggered laser pulse.

17. The device of claim 12, wherein the one or more pulse emission parameters include a signal for triggering a laser pulse and a current supplied to the at least one laser diode for generating a laser pulse.

\* \* \* \* \*